(12) United States Patent
Kanayama

(10) Patent No.: US 11,123,044 B2
(45) Date of Patent: Sep. 21, 2021

(54) SIGNAL PROCESSING DEVICE, ULTRASONIC DIAGNOSTIC APPARATUS, AND METHOD

(71) Applicant: Toshiba Medical Systems Corporation, Otawara (JP)

(72) Inventor: Yuko Kanayama, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 1139 days.

(21) Appl. No.: 15/353,086

(22) Filed: Nov. 16, 2016

(65) Prior Publication Data

US 2017/0150948 A1 Jun. 1, 2017

(30) Foreign Application Priority Data

Nov. 26, 2015 (JP) .............................. JP2015-230901

(51) Int. Cl.
*A61B 8/00* (2006.01)
*A61B 8/08* (2006.01)
*A61B 8/14* (2006.01)

(52) U.S. Cl.
CPC .............. *A61B 8/5215* (2013.01); *A61B 8/14* (2013.01); *A61B 8/461* (2013.01); *A61B 8/469* (2013.01); *A61B 8/488* (2013.01); *A61B 8/5207* (2013.01); *A61B 8/56* (2013.01)

(58) Field of Classification Search
CPC ........... A61B 8/06; A61B 8/0883; A61B 8/14; A61B 8/461; A61B 8/463; A61B 8/469; A61B 8/481; A61B 8/488; A61B 8/5207; A61B 8/5215; A61B 8/5246; A61B 8/56; G01S 7/52033; G01S 7/52036; G01S 7/52038; G01S 7/52039; G01S 7/52071
See application file for complete search history.

(56) References Cited

U.S. PATENT DOCUMENTS

2010/0249590 A1  9/2010 Kanayama et al.
2014/0114189 A1* 4/2014 Kanayama .......... G01S 7/52046
                                                600/438
(Continued)

FOREIGN PATENT DOCUMENTS

JP       60-31740       2/1985
JP       60-195473 A   10/1985
(Continued)

OTHER PUBLICATIONS

Japanese Office Action dated May 21, 2019 in Patent Application No. 2015-230901.
(Continued)

*Primary Examiner* — Christopher L Cook
(74) *Attorney, Agent, or Firm* — Oblon, McClelland, Maier & Neustadt, L.L.P.

(57) ABSTRACT

A signal processing device according to an embodiment includes adjustment circuitry and processing circuitry. The adjustment circuitry adjusts a received signal based on an echo of an ultrasonic wave transmitted to a subject with gain corresponding to a location at which the echo has been generated. The processing circuitry corrects the received signal that has been adjusted by the adjustment circuitry and calculates an index value relating to attenuation by using the corrected received signal.

19 Claims, 6 Drawing Sheets

(56) References Cited

U.S. PATENT DOCUMENTS

| | | | | |
|---|---|---|---|---|
| 2014/0243667 A1* | 8/2014 | Wilkening | ............... | A61N 7/00 600/438 |
| 2015/0374335 A1* | 12/2015 | Brown | ................ | G01S 15/8993 600/447 |
| 2016/0081662 A1* | 3/2016 | Denk | .................. | A61B 8/5207 600/437 |
| 2017/0086795 A1 | 3/2017 | Kanayama | | |
| 2017/0135672 A1* | 5/2017 | Pelissier | ................. | A61B 8/14 |

FOREIGN PATENT DOCUMENTS

| | | | |
|---|---|---|---|
| JP | 63-91783 | A | 4/1988 |
| JP | 63-130054 | | 6/1988 |
| JP | 64-5533 | A | 1/1989 |
| JP | 1-242043 | A | 9/1989 |
| JP | 7-51270 | | 2/1995 |
| JP | 2010-233859 | | 10/2010 |
| JP | 5747377 | | 7/2015 |
| JP | 2017-064183 | | 4/2017 |

OTHER PUBLICATIONS

Japanese Office Action dated Aug. 13, 2019 in Japanese Patent Application No. 2015-230901 (with English translation), 8 pages.

\* cited by examiner

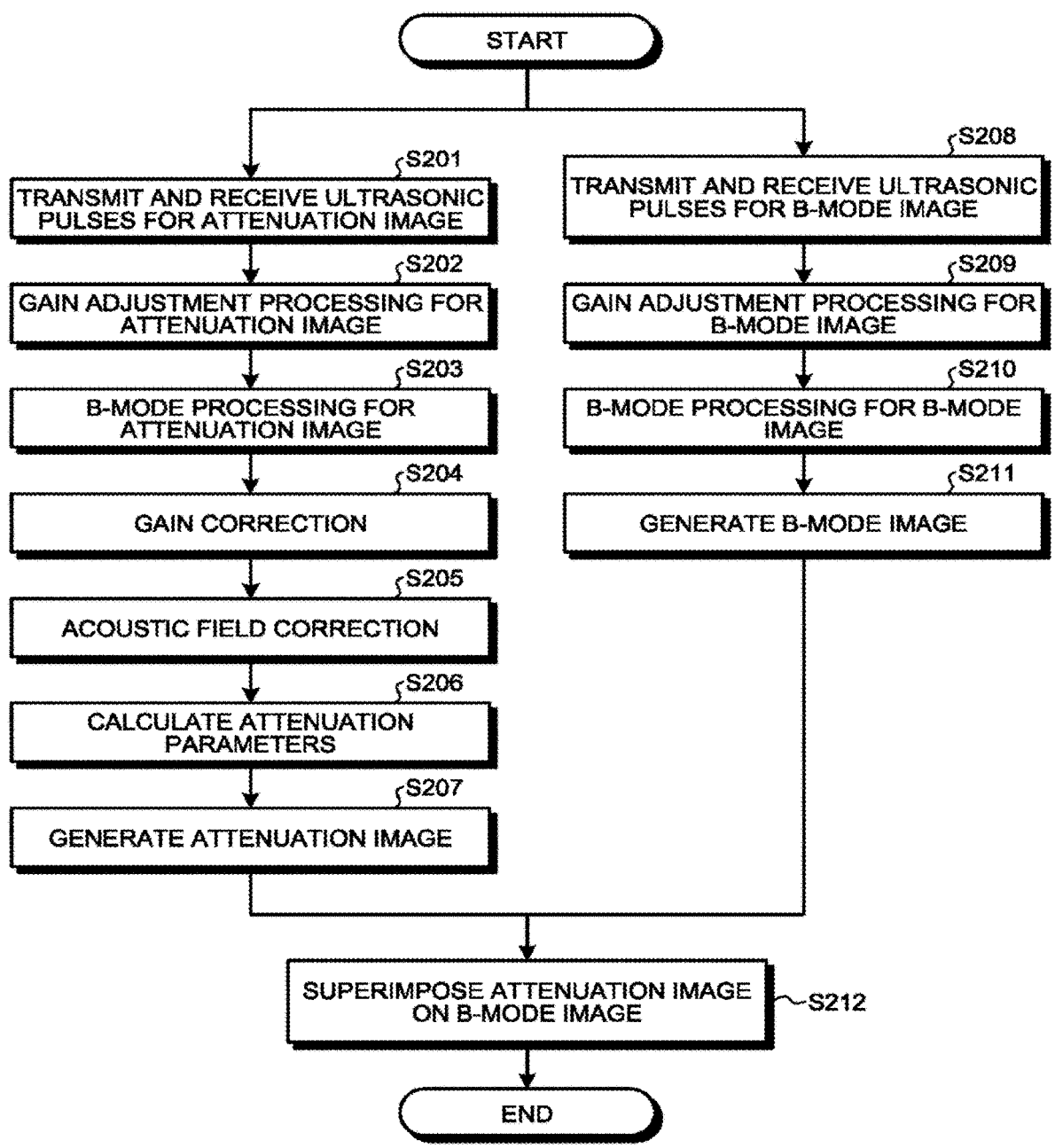

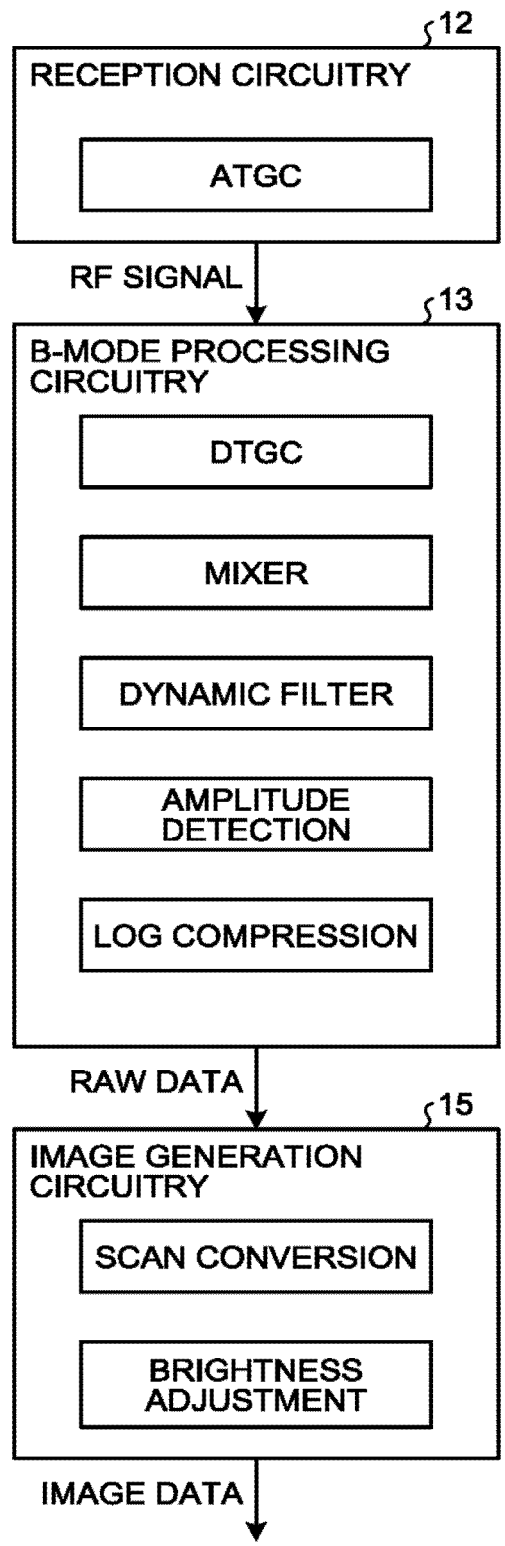

SIGNAL PROCESSING DEVICE, ULTRASONIC DIAGNOSTIC APPARATUS, AND METHOD

CROSS-REFERENCE TO RELATED APPLICATIONS

This application is based upon and claims the benefit of priority from Japanese Patent Application No. 2015-230901, filed on Nov. 26, 2015; the entire contents of which are incorporated herein by reference.

FIELD

Embodiments described herein relate generally to a signal processing device, an ultrasonic diagnostic apparatus, and a method.

BACKGROUND

Conventional ultrasonic diagnostic apparatuses display, for example, the amplitude of received signals of ultrasonic waves transmitted from an ultrasonic probe in terms of brightness to visualize the anatomy of a body tissue. The ultrasonic received signals contain various types of physical information in addition to the information on the anatomy of the body tissue. For example, observing the attenuation of the received signals allows an observer to estimate the characteristics of a body tissue. Specifically, when the received signals from the liver are significantly attenuated, it is suspected that the liver contains many lipid droplets and the subject has a fatty liver. When the subject suffers from liver cirrhosis, significantly attenuated signals may be received.

BRIEF DESCRIPTION OF THE DRAWINGS

FIG. 5 is a flowchart illustrating the process performed in an ultrasonic diagnostic apparatus according to a second embodiment;

FIG. 6 is a diagram illustrating gain adjustment processing according to another embodiment.

DETAILED DESCRIPTION

The following describes a signal processing device, an ultrasonic diagnostic apparatus, and a method according to embodiments with reference to the accompanying drawings. Embodiments are not limited to the embodiments described below. Descriptions in one embodiment are basically applicable to other embodiments in the same manner.

First Embodiment

Figure 1:
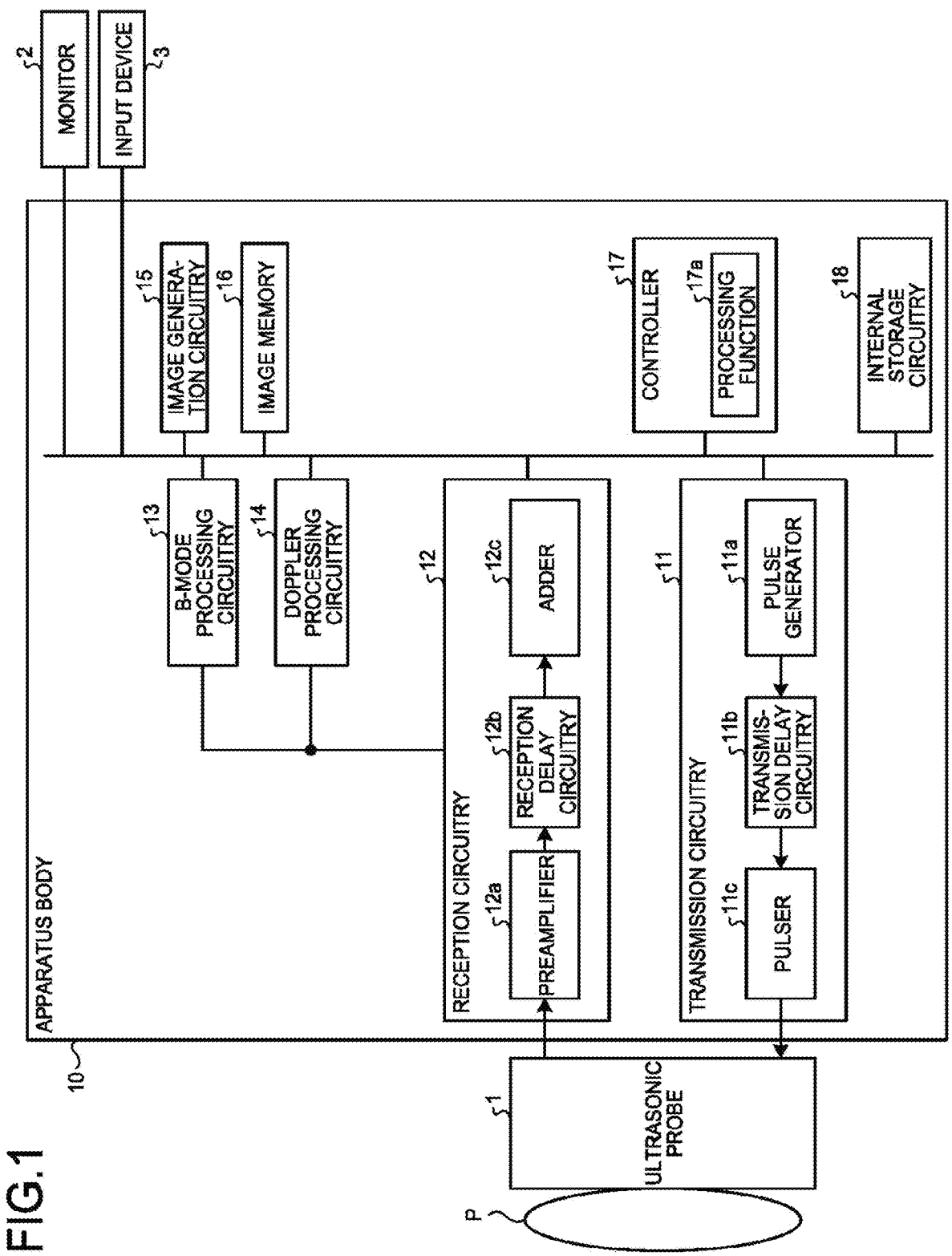
FIG. 1 is a diagram illustrating an example of a configuration of an ultrasonic diagnostic apparatus according to a first embodiment.

Described first is an example of a configuration of an ultrasonic diagnostic apparatus according to a first embodiment. FIG. 1 is a diagram illustrating an example of a configuration of the ultrasonic diagnostic apparatus according to the first embodiment. As illustrated in FIG. 1, the ultrasonic diagnostic apparatus according to the first embodiment includes an ultrasonic probe 1, a monitor 2, an input device 3, and an apparatus body 10.

The ultrasonic probe 1 includes a plurality of piezoelectric transducer elements. Each piezoelectric transducer element generates an ultrasonic wave based on a drive signal provided by later-described transmission circuitry 11 included in the apparatus body 10. The ultrasonic probe 1 receives returning signals from a subject P and converts them into electric signals. The ultrasonic probe 1 includes, for example, a matching layer and an acoustic lens provided on the piezoelectric transducer elements and a backing material that prevents propagation of ultrasonic waves from the piezoelectric transducer elements backwards. The ultrasonic probe 1 is detachably coupled to the apparatus body 10.

When the ultrasonic probe 1 transmits an ultrasonic wave to the subject P, the transmitted ultrasonic wave is subsequently reflected by discontinuities of acoustic impedance in inner tissues of the subject P, and the reflected waves are received by each of the piezoelectric transducer elements included in the ultrasonic probe 1 as received signals. The amplitude of a received signal depends on the difference in acoustic impedance between discontinuities by which the ultrasonic wave is reflected. When an ultrasonic pulse is transmitted and reflected by a surface of a moving blood flow or a moving cardiac wall, the received signal has been frequency-shifted (Doppler-shifted) due to the Doppler effect. The extent of the shift depends on a velocity component of the moving object relative to the transmitting direction of the ultrasonic pulse.

The first embodiment is applicable to a case in which the subject P is two-dimensionally scanned with a one-dimensional ultrasonic probe 1 including a plurality of piezoelectric transducer elements arranged in a row, a case in which the subject P is three-dimensionally scanned with a one-dimensional ultrasonic probe 1 including a mechanism that swings the piezoelectric transducer elements aligned in a row, and a case in which the subject P is three-dimensionally scanned with a two-dimensional ultrasonic probe 1 including a plurality of piezoelectric transducer elements that are two-dimensionally arranged in matrix. It is also possible for the one-dimensional ultrasonic probe to one-dimensionally scan the subject P with a single scan line, or for the two-dimensional ultrasonic probe to two-dimensionally scan the subject P by transmitting focused ultrasonic waves. In the following description, scan is performed with a one-dimensional ultrasonic probe 1 (also referred to as a 1D array probe) including a plurality of piezoelectric transducer elements arranged in a row.

The input device 3 includes, for example, a mouse, a keyboard, buttons, a panel switch, a touch command screen, a foot switch, and a trackball. The input device 3 receives various types of setting requests from an operator of the ultrasonic diagnostic apparatus and transfers the received setting requests to the apparatus body 10.

The input device 3 receives, from the operator, requests on, for example, setting of a region of interest (ROI) on which image processing is performed by image generation circuitry 15 to be described later, and setting of a sample volume as the ROI. The ROI received by the input device 3 will be described in detail later in the first embodiment.

The monitor 2 displays, for example, a graphical user interface (GUI) for allowing the operator of the ultrasonic diagnostic apparatus to input various types of setting requests by using the input device 3, or displays ultrasonic images generated in the apparatus body 10.

The apparatus body 10 generates ultrasonic images based on received signals received by the ultrasonic probe 1. As illustrated in FIG. 1, the apparatus body 10 includes the transmission circuitry 11, reception circuitry 12, B-mode processing circuitry 13, Doppler processing circuitry 14, the image generation circuitry 15, an image memory 16, a controller 17, and internal storage circuitry 18.

The transmission circuitry 11 includes a pulse generator 11a, transmission delay circuitry 11b, and a pulser 11c. The transmission circuitry 11 provides drive signals to the ultrasonic probe 1. The pulse generator 11a repeatedly generates a rate pulse for forming transmission ultrasonic waves at a certain pulse repetition frequency (PRF). The PRF is also referred to as a rate frequency. The transmission delay circuitry 11b gives transmission delay time to each rate pulse generated by the pulse generator 11a. The transmission delay time is applied to each piezoelectric transducer element to focus the ultrasonic waves generated by the ultrasonic probe 1 into a beam for each channel, which is necessary for determining transmission directivity. The transmission direction or the transmission delay time for determining the transmission direction is stored in the internal storage circuitry 18, and is referred to when the beam is transmitted. The pulser 11c applies a drive signal (a drive pulse) to the ultrasonic probe 1 at a timing based on the rate pulse. In other words, the transmission delay circuitry 11b gives different transmission delay time to each rate pulse to control the ultrasonic waves transmitted from the surfaces of the piezoelectric transducer elements to travel in certain directions. With this configuration, the transmission circuitry 11 controls the transmission directivity of the ultrasonic waves.

The transmission circuitry 11 has capability of instantly changing a transmission frequency, a transmission drive voltage, and other transmission properties under the instructions of the controller 17 to be described later to execute a certain scan sequence. Changing the transmission drive voltage, in particular, is implemented by linear amplifier oscillation circuitry that can instantly changing the voltage values, or a mechanism that electrically switches a plurality of power units.

The reception circuitry 12 includes a preamplifier reception delay circuitry 12b, and an adder 12c. The reception circuitry 12 performs various types of processing on the received signals received by the ultrasonic probe 1 to generate echo data.

The preamplifier 12a performs gain adjustment processing to adjust received signals received via the ultrasonic probe 1 for each channel. In other words, the preamplifier 12a adjusts the received signals output from the piezoelectric transducer elements with gain. For example, the preamplifier 12a adjusts a received signal based on an echo of an ultrasonic wave transmitted to the subject P with gain corresponding to a location at which the echo has been generated. For example, the preamplifier 12a adjusts a received signal based on an echo of an ultrasonic wave transmitted to the subject P with gain corresponding to a depth level. The gain adjustment processing performed by the preamplifier 12a will be described later. The preamplifier 12a is an example of adjustment circuitry.

The reception circuitry 12 includes an analog to digital (A/D) converter, which is not illustrated. The A/D converter converts gain-corrected received signals from analog to digital. The reception delay circuitry 12b gives digital data the reception delay time necessary for determining reception directivity. In other words, the reception delay circuitry 12b performs delay processing on a plurality of received signals that have been adjusted by the preamplifier 12a. The adder 12c performs addition processing on the received signals that have been processed by the reception delay circuitry 12b. In other words, the adder 12c performs addition processing on a plurality of received signals that have been adjusted by the preamplifier 12a The addition processing performed by the adder 12c enhances reflection components of the received signals from directions based on the reception directivity. With this configuration, the reception circuitry 12 controls the reception directivity in receiving the ultrasonic waves.

The B-mode processing circuitry 12 receives echo data generated by the reception circuitry 12 and performs processing such as logarithm amplification, envelope detection, and logarithmic compression on the received echo data to generate data (B-mode data) in which signal intensity is represented by a degree of brightness.

The Doppler processing circuitry 14 receives echo data generated by the reception circuitry 12 and performs frequency analysis on the received echo data to extract Doppler shift (Doppler shift frequency). The Doppler processing circuitry 14 uses the Doppler shift to extract echo components affected by the Doppler effect from blood flow, tissues, or contrast agent, and to generate data (Doppler data) of moving object information such as an average velocity, variance, and power that has been extracted with respect to many points or a single point.

The B-mode processing circuitry 13 and the Doppler processing circuitry 14 include quadrature detector circuitry, which is not illustrated. The quadrature detector circuitry converts an output signal from the adder 12c into an in-phase signal (I signal) and a quadrature-phase signal (Q signal) in baseband. The B-mode processing circuitry 13 uses the I signal and the Q signal (hereinafter referred to as I/Q, signals) as the echo data, and performs processing such as logarithm amplification, envelope detection, and logarithmic compression on the echo data to generate B-mode data. The Doppler processing circuitry 14 uses the I/Q signals as the echo data, and performs frequency analysis on the echo data to generate Doppler data.

The image generation circuitry 15 generates image data for display from the data generated by the B-mode processing circuitry 13 and the Doppler processing circuitry 14. In other words, the image generation circuitry 15 generates a B-mode image from the B-mode data generated by the B-mode processing circuitry 13. The B-mode image is composed of received signals, the intensity of which is represented by degrees of brightness. The image generation circuitry 15 generates a color Doppler image from the Doppler data generated by the Doppler processing circuitry 14. The color Doppler image includes a velocity image, a dispersion image, a power image or any combinations thereof each representing moving object information on blood flow (blood flow information). For example, the image generation circuitry 15 generates a power image that displays the blood flow information in red tones corresponding to the levels of power. In addition to the color Doppler image for a color display, the image generation circuitry 15 can generate, for example, a gray-scale power image in which the degree of brightness is represented in gray scale in accordance with the levels of the power.

The image generation circuitry 15 generates Doppler waveforms from the Doppler data generated by the Doppler processing circuitry 14. The Doppler waveforms represent speed information on the blood flow plotted over time.

Specifically, the image generation circuitry 15 generates a time-varying curve with the vertical axis representing the velocity of the blood flow in a sample volume and the horizontal axis representing time. The image generation circuitry 15 sets a range in the vertical axis direction in accordance with the variance of the blood flow in the sample volume and sets brightness values in accordance with the power values of the blood flow in the sample volume.

The image generation circuitry 15 ordinarily converts (scan-converts) a sequence of scan-line signals of ultrasonic scan into a sequence of scan-line signals in a video format typically used for, for example, televisions, and generates an ultrasonic image (B-mode image or blood flow image) as a display image. Specifically, the image generation circuitry 15 performs coordinates transformation in accordance with the mode of ultrasonic scan of the ultrasonic probe 1, and generates the ultrasonic image as a display image. The image generation circuitry 15 performs various types of image processing in addition to scan conversion. For example, the image generation circuitry 15 performs image processing using a plurality of image frames after the scan conversion to regenerate an image of averaged brightness values (smoothing processing). For another example, the image generation circuitry 15 performs image processing using a differential filter in an image (edge enhancement processing).

When the ultrasonic waves are two-dimensionally transmitted and received, the image generation circuitry 15 performs coordinates transformation to generate a two-dimensional B-mode image or a two-dimensional blood flow image as a display image. When the ultrasonic waves are three-dimensionally transmitted and received, the image generation circuitry 15 generates volume data (three-dimensional B-mode image or three-dimensional blood flow image), and performs various types of rendering processing on the volume data to generate, from the volume data, a two-dimensional image to be displayed on the monitor 2.

The image generation circuitry 15 combines information such as character information of various parameters, a scale, and a body mark with these images to generate composite images. The image generation circuitry 15 generates various superimposed images composed of any combination of the images, such as a superimposed image of the B-mode image and the color Doppler image. The image generation circuitry 15 generates an image including different types of images displayed side by side.

The image memory 16 stores therein various types of data generated by the image generation circuitry 15. The image memory 16 can store therein data (raw data) generated by the B-mode processing circuitry 13 or the Doppler processing circuitry 14. The image memory 16 can store therein echo data generated by the reception circuitry 12 as necessary.

The internal storage circuitry 18 stores therein control programs for performing transmission and reception of ultrasonic waves, image processing, and display processing, and stores various types of data such as diagnostic information (patient IDs, doctor's opinions, for example), diagnostic protocols, and various body marks. The internal storage circuitry 18 is also used to store, for example, data stored in the image memory 16 as necessary. The data stored in the internal storage circuitry 18 can be transferred to an external peripheral via an interface, which is not illustrated.

The controller 17 controls the entire processing of the ultrasonic diagnostic apparatus. Specifically, the controller 17 controls processing of the transmission circuitry 11, the reception circuitry 12, the B-mode processing circuitry 13, the Doppler processing circuitry 14, and the image generation circuitry 15 in accordance with setting requests input from the operator through the input device 3, and control programs and data read from the internal storage circuitry 18. The controller 17 controls the monitor 2 to display data stored in the image memory 16 or GUIs for use by the operator to specify each type of processing.

The controller 17 executes a processing function 17a illustrated in FIG. 1. Functions performed by the processing function 17a that is a component of the controller 17 illustrated in FIG. 1 are stored in the internal storage circuitry 18 as computer programs in a computer-executable format. The controller 17 is a processor that reads the computer programs from the internal storage circuitry 18 and executes them to implement functions corresponding to the respective computer programs. In other words, the controller 17 that has read a computer program has the function of the program in the controller 17 in FIG. 1. The processing function 17a is also referred to as processing circuitry.

The entire configuration of the ultrasonic diagnostic apparatus according to the first embodiment has been described. The ultrasonic diagnostic apparatus according to the first embodiment configured as such visualizes, in an ordinary operation, the anatomy of a body tissue by representing the amplitude of echo data in terms of brightness by the B-mode processing circuitry 13, and visualizes moving object information by performing frequency analysis on the echo data by the Doppler processing circuitry 14. However, the ultrasonic received signals contain various types of physical information in addition to the anatomical information on a body tissue or the moving object information.

For example, each body tissue has a specific attenuation characteristic. A technique for quantifying attenuation of an echo by using an ultrasonic received signal is known. An ultrasonic wave transmitted to the subject P propagates in the body while being attenuated. If the ultrasonic wave is largely attenuated, no signal may be received that is strong enough to be used as a received signal. In another aspect, observing the attenuation of received signals allows the observer to obtain the characteristics of the body tissue. Specifically, when the received signals derived from the liver of the subject P are significantly attenuated, it is suspected that the liver contains many lipid droplets and the subject P has a fatty liver. In an observation of a subject P who suffers from liver cirrhosis, the received signals are, in some cases, significantly attenuated as well.

Some techniques have been disclosed for quantifying the extent of attenuation of ultrasonic waves. It is known that, for example, the extent of attenuation of ultrasonic waves in a biological body varies with the frequency. A method for obtaining the value specific to a monitored tissue is known. This method compares changes in intensity of a plurality of signals having different frequencies. In this method, a plurality of ultrasonic pulses having different center frequencies are transmitted and received, and changes in intensity of the received signals are compared with respect to the depth levels. With this method, the extent of attenuation specific to the subject P is estimated. Moreover, a method for displaying more diverse anatomical characteristics is known. In this method, attenuation coefficients for the respective frequencies are obtained, and the ratios of the obtained attenuation coefficients are displayed.

As another technique, a method of transmitting and receiving one ultrasonic pulse wave having a wide bandwidth is known. In this method, the ultrasonic pulse is transmitted in each direction to obtain the same effect as that of the method of transmitting and receiving a plurality of ultrasonic pulses having different center frequencies. However, this method using wide-band pulse generates a signal having high-frequency components when a low-frequency range signal propagates within the tissue, and such a high-frequency signal may cause errors in estimating the attenuation specific to the subject P. To solve this problem, a method has been developed in which two ultrasonic pulses whose polarity is inverted are transmitted in a single direction, and a difference calculation is performed on the resulting received signals to eliminate the high-frequency components that have been generated during propagation and estimate the attenuation specific to the subject P.

However, such conventional techniques are based on transmitting and receiving ultrasonic waves having different frequencies. Such technologies require a more complicated circuit than a circuit that processes transmission and reception signals to obtain an ordinary B-mode image. Thus, installing a new signal processing circuit for quantifying the attenuation of echoes in the ultrasonic diagnostic apparatus may result in a further increase in the size and the cost of the ultrasonic diagnostic apparatus.

In the first embodiment, the controller 17 executes the processing function 17a to quantify the attenuation of echoes by a simple configuration. In other words, the processing function 17a corrects a received signal that has been adjusted by the preamplifier 12a in accordance with gain, and calculates an index value relating to attenuation by using the corrected received signal. For example, the processing function 17a corrects a received signal after delay addition processing in accordance with gain, and calculates an index value by using the corrected received signal. The following describes the process performed in the ultrasonic diagnostic apparatus according to the first embodiment with reference to FIG. 2.

Figure 2:
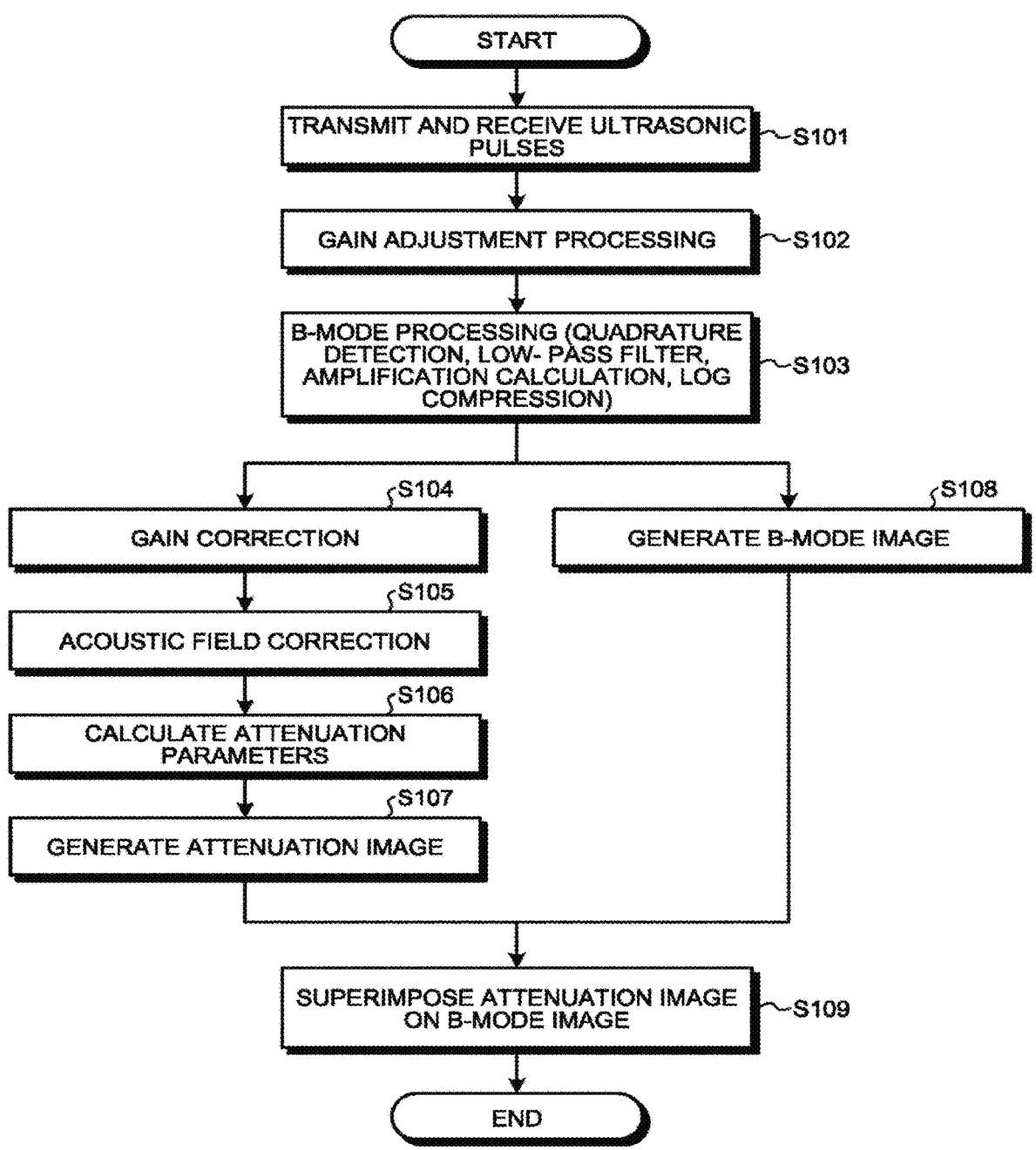
FIG. 2 is a flowchart illustrating the process performed in the ultrasonic diagnostic apparatus according to the first embodiment.

FIG. 2 is a flowchart illustrating the process performed in the ultrasonic diagnostic apparatus according to the first embodiment. The process illustrated in FIG. 2 describes ultrasonic scan for quantifying attenuation of echoes with no contrast agent administered to the subject P. The flowchart in FIG. 2 illustrates operations performed in the ultrasonic diagnostic apparatus according to the first embodiment as a whole. In the description hereof, which component of the ultrasonic diagnostic apparatus performs which step of the flowchart will be explained.

Step S101 is performed by the ultrasonic probe 1. At Step S101, the ultrasonic probe 1 transmits and receives ultrasonic pulses. For example, when the input device 3 receives, from the operator, a setting of "attenuation quantification mode", which is a scan mode for quantifying the attenuation of echoes, the controller 17 sets ultrasonic transmission conditions for the attenuation quantification mode t the transmission circuitry 11. The transmission circuitry 11 then sets the ultrasonic transmission conditions in accordance with the setting for the attenuation quantification mode, and ultrasonic waves are transmitted to the subject P from the ultrasonic probe 1. As an ultrasonic transmission condition for the attenuation quantification mode, the transmission bandwidth is determined based on the frequency characteristic of the probe. For example, the transmission bandwidth of the pulse is a narrow bandwidth including the center frequency. Specifically, the transmission bandwidth of the pulse is a narrow bandwidth including a single frequency, and is determined depending on the subject region to be monitored. When, for example, the subject region is abdomen, the transmission bandwidth is to 3 MHz. The transmitted ultrasonic pulses are scattered by structures in the subject P, and received by the ultrasonic probe 1.

Step S102 is performed by the preamplifier 12a. At Step S102, the preamplifier 12a performs gain adjustment processing. For example, the received signals output from the ultrasonic probe 1 are transmitted to the reception circuitry 12. The preamplifier 12a in the reception circuitry 12 performs the gain adjustment processing on the received signals. The preamplifier 12a adjusts the received signals by using gain that varies with time response that has been determined in advance.

Specifically, the preamplifier 12a performs the gain adjustment processing for the following three purposes. That is, the preamplifier 12a performs first gain adjustment processing to compensate for the lack of depth sensitivity, second gain adjustment processing to reduce excessive shallow sensitivity, and third gain adjustment processing to achieve the purposes of the first and second gain adjustment processing. For example, in the first gain adjustment processing, the preamplifier 12a sets the gain with respect to a received signal based on an echo coming from a greater depth to larger than one. In the second gain adjustment processing, the preamplifier 12a sets the gain with respect to a received signal based on an echo coming from a shallow depth to smaller than one. In the third gain adjustment processing, the preamplifier 12a sets the gain with respect to a received signal based on an echo coming from a greater depth to larger than one, and sets the gain with respect to a received signal based on an echo coming from a shallow depth to smaller than one.

Figure 3:
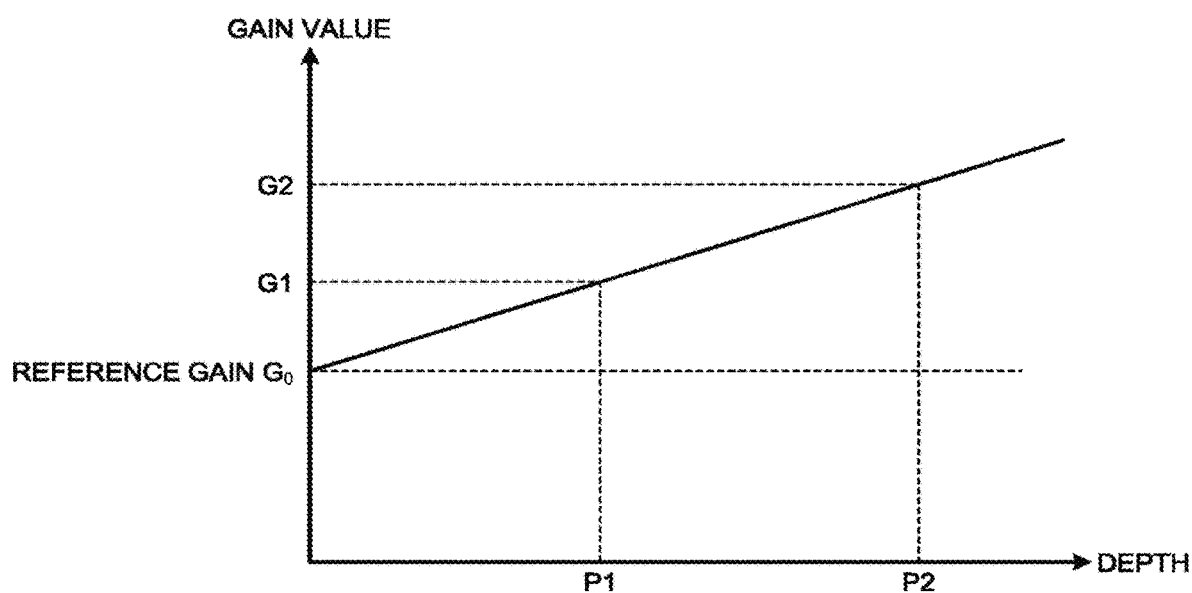
FIG. 3 is a graph for explaining gain adjustment processing according to the first embodiment.

An example of the gain adjustment processing will be described with reference to FIG. 3. FIG. 3 is a graph for explaining the gain adjustment processing according to the first embodiment. With reference to FIG. 3, the first gain adjustment processing for compensating for the lack of depth sensitivity is described.

The horizontal axis in FIG. 3 represents depth and the vertical axis in FIG. 3 represents the gain value. In the example illustrated in FIG. 3, a reference gain G0 is set. The reference gain G0 indicates a reference adjustment value without regard to the location at which the echo has been generated. In the example in FIG. 3, G0>1. The gain value is adjusted from the reference gain G0 in accordance with the location at which the echo has been generated. As illustrated in FIG. 3, for example, the gain value increases with the depth of the location at which the echo has been generated. For example, the echo generated at a location of depth P1 corresponds to a gain value G1, and the echo generated at a location at depth P2 corresponds to a gain value G2. That is, at the depth P1, the adjustment value corresponding to the location at which the echo has been generated is calculated as G1–G0, and at the depth P2, the adjustment value of the location at which the echo has been generated is calculated as G2–G0. As described above, the gain value varies in accordance with the location at which the echo has been generated. In other words, the preamplifier 12a changes the gain value in accordance with the time response that has been determined in advance. The time response of a gain by which a reception signal is multiplied in the preamplifier 12a is stored in the internal storage circuitry 18.

Step S103 is performed by the B-mode processing circuitry 13. At Step S103, the B-mode processing circuitry 13 performs B-mode processing on the received signals that have been adjusted by the preamplifier 12a For example, the gain-adjusted received signals are transmitted to the reception delay circuitry 12b and to the adder 12c, at which beam forming processing is performed, and are transmitted to the B-mode processing circuitry 13. The B-mode processing circuitry 13 performs B-mode processing such as quadrature detection, low-pass filter, amplification calculation, and log compression on the gain-adjusted received signals. To correctly measure the ultrasonic attenuation within the subject P, the B-mode processing circuitry 13 limits the reception bandwidth to a narrow bandwidth around the transmission center frequency. This configuration allows the B-mode processing circuitry 13 to remove tissue harmonic signal components.

The B-mode processing circuitry 13 makes no change to the reception bandwidth at each depth level. In some cases, for example, the B-mode processing circuitry 13 is set to detect a lower-frequency band region depending on the depth of the location at which the echo has been generated because a higher-frequency echo is more significantly attenuated. In the attenuation quantification mode, however, the B-mode processing circuitry 13 makes no change to the reception bandwidth at each depth level, and sets the reception bandwidth to a narrow bandwidth around the transmission center frequency. B-mode data generated by the B-mode processing circuitry 13 is referred to as raw data.

Step S104 is performed by the processing function 17a. At Step S104, the processing function 17a performs gain correction processing on the raw data. The gain correction processing is performed to cancel the gain adjustment to the raw data based on the time response of the gain stored in the internal storage circuitry 18. For example, the processing function 17a corrects a received signal that has been adjusted by the preamplifier 12a such that the processing function 17a cancels an adjustment value with which the preamplifier 12a has adjusted the received signal. In other words, the processing function 17a performs correction on the raw data such that it cancels both reference gain and adjustment value corresponding to a location at which an echo has been generated.

For example, the processing function 17a may be configured to correct a received signal that has been adjusted by the preamplifier 12a such that the processing function 17a equalizes an adjustment value with which the preamplifier 12a has adjusted the received signal. The adjustment value corresponds to the location (depth) at which the echo has been generated. In other words, the processing function 17a performs correction on the raw data such that the processing function 17a equalizes adjustment values corresponding to different depth levels at which the echoes have been generated. In this case, the processing function 17a does not cancel the adjustment value based on the reference gain.

Step S105 is performed by the processing function 17a. At Step S105, the processing function 17a performs acoustic field correction processing. For example, the processing function 17a performs acoustic field correction processing to cancel an effect of the acoustic field on the basis of acoustic field data stored in the internal storage circuitry 18. In other words, the processing function 17a corrects a received signal that has been adjusted by the preamplifier 12a in accordance with an acoustic field determined by at least one of a transmission condition of the ultrasonic wave and a reception condition of the echo. Specifically, performing transmit focusing on the ultrasonic waves in transmission varies the intensity of the transmitted ultrasonic waves between the focal position and other positions out of the focal position in the same scan line. In the acoustic field correction, the processing function 17a corrects the received signal such that the transmitted ultrasonic waves at the focal position have the same intensity as that of the transmitted ultrasonic waves at other positions out of the focal position in the same scan line. The acoustic field data is determined by the ultrasonic probe 1 or in accordance with transmission and reception conditions including, for example, frequency, focusing, and opening. Acoustic field data corresponding to possible conditions is stored in the internal storage circuitry 18 in advance. After the gain correction processing at Step S104 and the acoustic field correction processing at Step S105, the processing function 17a obtains ultrasonic received signals on which only distribution information on scatters and attenuation information on a tissue are reflected.

Step S106 is performed by the processing function 17a. At Step S106, the processing function 17a calculates attenuation parameters. In other words, the processing function 17a calculates an attenuation parameter by using a received signal that has been corrected in accordance with the gain and the acoustic field. For example, supposing that the scatters in a tissue are uniformly distributed, the processing function 17a detects the change of the corrected ultrasonic received signal in the depth direction and calculates the attenuation parameter of the ultrasonic wave at each location in the depth direction. For example, the processing function 17a calculates a gradient of an ultrasonic received signal in the depth direction within a certain depth range, and the calculated gradient in the depth direction is multiplied by the transmission and reception frequency, whereby an attenuation constant (dB/cm/MHz) is calculated as the attenuation parameter. The attenuation parameter is an example of an index value.

Step S107 is performed by the image generation circuitry 15. At Step S107, the image generation circuitry 15 generates an attenuation image. In other words, the processing function 17a generates an attenuation image based on attenuation parameters corresponding to a plurality of locations at which echoes have been generated. For example, upon calculating attenuation constants with respect to the locations in a scan range, the image generation circuitry 15 generates an attenuation image that visualizes the attenuation constants with respect to the locations on the basis of a color map set in advance and calculation results of the attenuation constants. The image generation circuitry 15 generates the attenuation image by using received signals based on the echoes of ultrasonic waves transmitted in a narrow transmission bandwidth including the center frequency. The image generation circuitry 15 may generate the attenuation image as a color image or may generate it in gray scale.

Step S108 is performed by the image generation circuitry 15. At Step S108, the image generation circuitry 15 generates a B-mode image based on the raw data generated. Step S103.

Figure 4:
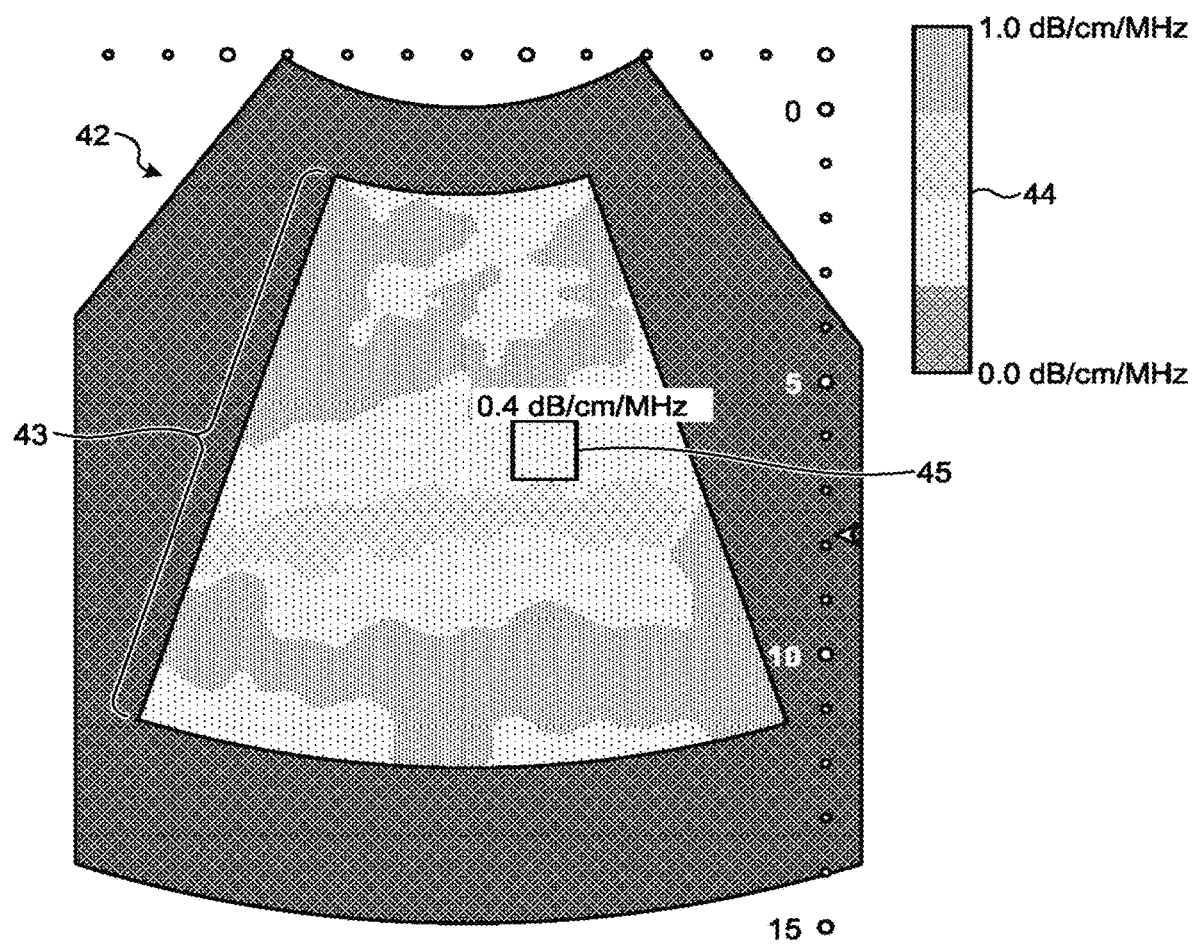
FIG. 4 is a diagram illustrating an example of a superimposed image according to the first embodiment.

Step S109 is performed by the image generation circuitry 15. At Step S109, the image generation circuitry 15 displays the B-mode image and the attenuation image that have been generated based on the received signals from a single scanned section as a superimposed image. For example, the image generation circuitry 15 combines the attenuation image generated at Step S107 and the B-mode image generated at Step S108 to generate a superimposed image. The image generation circuitry 15 displays the generated superimposed image on the monitor 2. FIG. 4 is a diagram illustrating an example of the superimposed image according to the first embodiment.

FIG. 4 illustrates an example of a superimposed image in an observation of a uniform phantom having an attenuation constant of 0.5 dB/cm/MHz. The superimposed image illustrated in FIG. 4 includes an attenuation image 43 superimposed on a B-mode image 42. The attenuation image 43 is generated by using attenuation parameters with respect to the locations within an ROI set on, for example, the B-mode image 42. As illustrated in FIG. 4, values of the attenuation constants are associated with colors by a color map 44. With this configuration, the operator can see a spatial distribution of the attenuation constants by referring to the attenuation image 43.

An ROI 45 for measurement may be set on the attenuation image 43 through the input device 3. In this case, a representative value of the attenuation parameters in the measurement ROI 45 may be additionally displayed in a numerical value. In other words, the processing function 17a calculates the representative value by using the attenuation parameters corresponding to the locations at which echoes have been generated, and displays the calculated representative value on the monitor 2. The representative value is, for example, a mean value of the attenuation constants in the measurement ROI 45. In the example in FIG. 4, a numerical value of 0.4 db/cm/MHz is displayed to indicate the representative value of the attenuation constants in the measurement ROI 45. The representative value may be a maximum value or a minimum value of the attenuation constants in the measurement ROI 45.

In the first embodiment described above, attenuation of echoes can be quantified with a simple configuration.

Although, in the first embodiment, the processing at Step S103 is performed by the B-mode processing circuitry 13, embodiments are not limited to this. The processing at Step S103 may be performed by the processing function 17a, for example. Although, in the first embodiment, the processing from Step S107 to Step S109 is performed by the image generation circuitry 15, embodiments are not limited to this. The processing from Step S107 to Step S109 may be performed by the processing function 17a, for example. In other words, the processing function 17a may generate the B-mode image by using the received signals that have been adjusted by the preamplifier 12a, superimpose the attenuation image on the generated B-mode image, and display the superimposed image on the monitor 2.

Second Embodiment

In the first embodiment, the attenuation image and the B-mode image are generated from the same received signals. The transmission and reception signals for the attenuation image are set within a narrow bandwidth excluding tissue harmonic signals. Such transmission and reception signals for the attenuation image, when used for generating a B-mode image, may result in lower spatial resolution or lower contrast resolution of the B-mode image.

If ultrasonic waves different from those for quantifying the attenuation are transmitted and received to generate a B-mode image, transmission and reception of ultrasonic waves for generating the B-mode image are no longer relevant to the accuracy of the quantification of attenuation. In this case, ultrasonic waves in a wider bandwidth can be transmitted and received, and received signals can contain tissue harmonic signals to generate the B-mode image, thereby enhancing visibility of the B-mode image in the background. In a second embodiment, ultrasonic waves different from the ultrasonic waves for quantifying the attenuation are transmitted and received for generating the B-mode image.

The configuration of the ultrasonic diagnostic apparatus according to the second embodiment is the same as the ultrasonic diagnostic apparatus according to the first embodiment illustrated in FIG. 1 except a part of the functions of the controller 17 and a part of the functions of the processing function 17a executed by the controller 17. Thus, the configuration of the ultrasonic diagnostic apparatus according to the second embodiment is not fully described except the configuration of the controller 17 and the processing function 17a.

FIG. 5 is a flowchart illustrating the process performed in the ultrasonic diagnostic apparatus according to the second embodiment. The flowchart in FIG. 5 illustrates operations performed in the ultrasonic diagnostic apparatus according to the second embodiment as a whole. In the description hereof, which component of the ultrasonic diagnostic apparatus performs which step of the flowchart will be explained. In FIG. 5, the processing from Step S201 to Step S207 corresponds to the processing from Step S101 to Step S107 in FIG. 2, respectively. Thus, the processing from Step S201 to Step S207 will not be fully described here.

Step S208 is performed by the ultrasonic probe 1. At Step S208, the ultrasonic probe 1 transmits and receives ultrasonic pulses for the B-mode image. At Step S208, the ultrasonic probe 1 transmits ultrasonic waves having a frequency band different from that of the ultrasonic waves transmitted at Step S101 or Step S201. For example, the ultrasonic probe 1 transmits wide-band ultrasonic waves. In the example of FIG. 5, the ultrasonic probe 1 performs the pulse inversion (PI) technique to extract tissue harmonic signals. In other words, the ultrasonic probe 1 transmits ultrasonic waves twice. In the second transmission, the ultrasonic probe 1 transmits ultrasonic waves having a waveform phase-shifted by 180 degrees (phase-inverted waveform) with respect to the waveform of the ultrasonic waves in the first. transmission. The ultrasonic probe 1 generates echo data in the first and the second transmissions. The ultrasonic probe 1 may extract a tissue harmonic signal by using techniques other than the PI technique, such as the amplitude modulation (AM) or the amplitude modulation phase modulation (AMPM).

Step S209 is performed by the preamplifier 12a. At Step S209, the preamplifier 12a performs the gain adjustment processing in the same manner as in Step S102 and Step S202.

Step S210 is performed by the B-mode processing circuitry 13. At Step S210, the B-mode processing circuitry 13 extracts a tissue harmonic signal by using, for example, the PI technique to improve the spatial resolution and the contrast resolution. Wide-band signals from greater depths are more likely to be attenuated, and thus the B-mode processing circuitry 13 may detect signals in a lower-band region with respect to the received signals coming from such greater depths.

Step S211 is performed by the image generation circuitry 15. At Step S211, the image generation circuitry 15 generates a B-mode image based on the raw data generated at Step S210. The image generation circuitry 15 generates, at Step S207, an attenuation image by using a received signal having a narrower bandwidth than a bandwidth of frequency components used for generating the B-mode image in the received signal that has been adjusted by the preamplifier 12a.

Step S212 is performed by the image generation circuitry 15. At Step S212, the image generation circuitry 15 combines, for example, the attenuation image generated at Step S207 and the B-mode image generated at Step S211 to generate a superimposed image.

In the second embodiment as described above, ultrasonic waves for generating the B-mode image are transmitted and received separately from the ultrasonic waves transmitted and received for generating the attenuation image. With this configuration, transmission and reception of ultrasonic waves for generating the B-mode image are no longer relevant to the accuracy of the quantification of attenuation. Thus, ultrasonic waves in a wider bandwidth can be transmitted and received, and received signals can contain tissue harmonic signals, for example. According to the second embodiment, the visibility of the B-mode image in the background can be improved.

According to the second embodiment, the spatial resolution and the contrast resolution of the B-mode image on which the attenuation image is superimposed can be improved. Thus, the operator can more easily read the color information of the attenuation parameters on a structure such as a tumor. Moreover, the operator can more easily recognize the target region in setting a measurement ROI, and thus the operator can more accurately set the measurement ROI.

Although the ultrasonic diagnostic apparatus according to the second embodiment transmits ultrasonic waves for generating the B-mode image by using the PI technique to extract the tissue harmonic signals, embodiments are not limited to this. The ultrasonic diagnostic apparatus does not necessarily use the PI technique in transmitting ultrasonic waves, or receive tissue harmonic signals to generate the B-mode image. For example, the ultrasonic diagnostic apparatus may use fundamental components in transmitting and receiving ultrasonic waves for generating the B-mode image in the same manner as transmitting and receiving ultrasonic waves for quantifying the attenuation. In this case, the ultrasonic diagnostic apparatus transmits and receives the ultrasonic waves for generating the B-mode image separately from the ultrasonic waves for quantifying attenuation. The ultrasonic diagnostic apparatus then, for example, uses higher-frequency components to generate a B-mode image, or increases the shift of the reception center frequency between a shallow and a greater depth to improve depth sensitivity. With this configuration, the ultrasonic diagnostic apparatus can improve the image quality of the B-mode image.

Although, in the second embodiment, the processing at Step S210 is performed by the B-mode processing circuitry 13, embodiments are not limited to this. The processing at Step S210 may be performed by the processing function 17a, for example. Although, in the second embodiment, the processing at Step S211 and processing at Step S212 are performed by the image generation circuitry 15, embodiments are not limited to this. The processing at Step S211 and Step S212 may be performed by the processing function 17a, for example. In this case, the processing function 17a generates the B-mode image by using received signals different from the received signals for generating the attenuation image, superimposes the attenuation image on the generated B-mode image, and displays the superimposed image on the monitor 2.

Modifications of Second Embodiment

Although, in the second embodiment described above, ultrasonic waves for generating the B-mode image are transmitted and received separately from the ultrasonic waves for quantifying the attenuation, embodiments are not limited to this. For example, ultrasonic waves commonly used for generating the B-mode image and for quantifying attenuation may be transmitted once. In this case, for example, received signals after the addition processing by the adder 12c are separated into a reception band of the ultrasonic waves for generating the B-mode image and a reception band of the ultrasonic waves for quantifying attenuation. Specifically, the B-mode processing circuitry 13 separates a single received signal received by the ultrasonic probe 1 into a reception band of the ultrasonic wave for generating the B-mode image and a reception band of the ultrasonic wave for quantifying attenuation, and generates raw data for generating the B-mode image and raw data for quantifying the attenuation. The processing function 17a performs the gain correction processing and the acoustic field correction processing on the raw data for quantifying attenuation, and calculates attenuation parameters. With this configuration, the ultrasonic diagnostic apparatus generates an attenuation image and a B-mode image each having a different reception band by using the same transmission and reception signals. This configuration eliminates repetition of scan processes for the same section with two types of transmission pluses, thereby increasing the frame rate.

When the ultrasonic diagnostic apparatus generates an attenuation image and a B-mode image each having a different reception band by using the same transmission and reception signals, the ultrasonic diagnostic apparatus can select transmission of wide-band ultrasonic waves or transmission of narrow-band ultrasonic waves including the center frequency. When, for example, wide-band ultrasonic waves are transmitted, the reception bandwidth for quantifying the attenuation is set to a narrow bandwidth around the transmission center frequency, whereas the reception bandwidth for generating the B-mode image is set to a wide bandwidth. When, for example, narrow-band ultrasounds are transmitted, the reception bandwidth for quantifying the attenuation is set to a narrow bandwidth around the center frequency, and the reception bandwidth for generating the B-mode image is set to a bandwidth of harmonic components having a frequency twice the transmission frequency. Although, in the second embodiment, the B-mode processing circuitry 13 separates the reception band of the ultrasonic waves for generating the B-mode image from the reception band of the ultrasonic waves for quantifying the attenuation, embodiments are not limited to this. For example, the reception circuitry 12 may separate the reception band of the ultrasonic waves for generating the B-mode image from the reception band of the ultrasonic waves for quantifying the attenuation. If the reception circuitry 12 is configured to separate the reception bands, the reception circuitry 12 includes a first system for separating the reception band of the ultrasonic waves for generating the B-mode image and a second system for separating the reception band of the ultrasonic waves for quantifying the attenuation.

Other Embodiments

Embodiments are not limited to the first and second embodiments described above.

Although, in the first and second embodiments, the superimposed image of an attenuation image and a B-mode image is displayed on the monitor 2, embodiments are not limited to this. For example, the ultrasonic diagnostic apparatus may display the attenuation image on the monitor 2 alone. The ultrasonic diagnostic apparatus may display the attenuation image and the B-mode image side by side on the monitor without superimposing each other.

In the first and second embodiments, the reception circuitry 12 is disposed in the apparatus body 10 when the ultrasonic probe 1 is a one-dimensional ultrasonic probe including a plurality of piezoelectric transducer elements arranged in a row, but embodiments are not limited to this.

For example, the reception circuitry 12 may be disposed in the ultrasonic, probe 1 when the ultrasonic probe 1 is a one-dimensional ultrasonic probe.

Although, in the first and second embodiments, the ultrasonic probe 1 is a 1D array probe, embodiments are not limited to this. For example, the ultrasonic probe 1 may be a two-dimensional ultrasonic probe also referred to as "2D array probe") including a plurality of piezoelectric transducer elements that are two-dimensionally arranged in matrix. When, for example, the ultrasonic probe 1 is a 2D array probe, the reception circuitry 12 may be disposed in the ultrasonic, probe 1 or in the apparatus body 10 in the same manner as the 1D array probe.

Although, in the first and second embodiments, the preamplifier 12a is an example of the adjustment circuitry, and the gain adjustment processing is performed by an analog circuit, embodiments are not limited to this. For example, the gain adjustment processing may be performed by a digital circuit. FIG. 6 is a diagram illustrating the gain adjustment processing according to another embodiment.

FIG. 6 only illustrates the reception circuitry 12, the B-mode processing circuitry 13, and the image generation circuitry 15 in the apparatus body 10, and illustrates a signal and data transmitted between the circuits. "Analog time gain control (ATGC)" illustrated in FIG. 6 indicates analog gain adjustment processing performed by the preamplifier 12a in the reception circuitry 12. The received signals generated in the reception circuitry 12 are transmitted to the B-mode processing circuitry 13 as radio frequency (RF) signals.

"Digital time gain control (DTGC)" in the B-mode processing circuitry 13 indicates digital gain adjustment processing. "Mixer" indicates processing in which output signals after DTGC are multiplied by a reference signal having a sine component and multiplied by a reference signal having a cosine component. "Dynamic filter" indicates processing of removing unnecessary frequency components (such as harmonic component from each type of output signals from Mixer. "Amplitude detection" indicates envelope detection. "Log compression" indicates logarithmic compression. The B-mode processing circuitry 13 transmits data after log compression to the image generation circuitry 15 as raw data.

"Scan conversion" in the image generation circuitry 15 indicates scan conversion processing that converts the raw data into image data. "Brightness adjustment" indicates adjustment processing on display brightness of the image data.

In the apparatus body 10, gain adjustment can be performed in "DTGC" and "brightness adjustment" illustrated in FIG. 6 as well as in "ATGC". "Dynamic filter" and "log compression" in the apparatus body 10 may be configured to perform the gain adjustment. Thus, any one of "ATGC", "DTGC", "brightness adjustment", "dynamic filter", and "log compression" or any combination thereof may be configured as the adjustment circuitry.

When, for example, the ultrasonic probe 1 is a 1D array probe, the gain adjustment processing may be performed on the received signals after the delay addition processing. When the ultrasonic probe 1 is a two-dimensional ultrasonic probe, the gain adjustment processing may be performed on the received signals before the delay addition processing performed sub-array by sub-array, or may be performed on the received signals after the delay addition processing performed between the sub-arrays. When, for example, the ultrasonic probe 1 is a 2D array probe, the gain adjustment processing using an analog circuit is typically performed after the delay addition processing performed sub-array by sub-array in the probe and before the delay addition processing performed between the sub-arrays in the apparatus body 10. The gain adjustment processing may be performed on the received signals before the delay addition processing performed on sub-array by sub-array, or on the received signals after the delay addition processing performed between the sub-arrays.

Although, in the first and second embodiments, the processing function 17a calculates attenuation constants as attenuation parameters at Step S106 and Step S206, embodiments are not limited to this. For example, the processing function 17a may calculate other values that reflect attenuation than the attenuation coefficients as the attenuation parameters at Step S106 and Step S206. Specifically, the processing function 17a may calculate a gradient of the brightness of a received echo in the depth direction, which is not divided by the frequency, and calculate a value in a unit of dB/cm or dB/m as an attenuation parameter. The processing function 17a may use, for example, Neper instead of dB in the unit of the attenuation parameter.

Although, in the first and second embodiments, the B-mode processing circuitry 13 and the Doppler processing circuitry 14 include a quadrature detector, embodiments are not limited to this. For example, the reception circuitry 12 may include a quadrature detector. In this case, the quadrature detector in the reception circuitry 12 converts, for example, output signals from the adder 12c into I signals and Q signals. The quadrature detector transmits the I signals and the Q signals to the B-mode processing circuitry 13 and the Doppler processing circuitry 14. The B-mode processing circuitry 13 generates B-mode data by using the I signals and the Q signals, and the Doppler processing circuitry 14 generates Doppler data by using the I signals and the Q signals.

Although, in the first and second embodiments, the controller 17 executes the processing function 17a, embodiments are not limited to this. For example, the apparatus body 10 may be provided with attenuation parameter calculation circuitry, and the attenuation parameter calculation circuitry may be configured to execute the same function as the processing function 17a.

Quantification of Attenuation in Presence of Contrast Agent

Although, in the first and the second embodiments, quantification of attenuation is performed in the absence of any contrast agent, embodiments are not limited to this. For example, such quantification of attenuation can be applied to ultrasonic scan in which contrast agent is administered to the subject. For example, the operator analyzes the change in brightness after the administration of contrast agent with respect to a normal site and a lesion site. When the normal site and the lesion site are located at different depth levels, the change in brightness cannot be easily compared because attenuation of ultrasonic waves varies depending on the depth. For this reason, attenuation of ultrasonic waves with respect to the normal site and the lesion site is quantified before the contrast agent is administered. This operation enables the operator who analyzes the change in brightness to correct the attenuation of ultrasonic waves and compare the change in brightness after the administration of the contrast agent.

The normal site and the lesion site may take different amounts of contrast agent in some cases. When the operator checks a test site that is known to vary the attenuation in accordance with the amount of contrast agent that the test site takes, the operator quantifies the attenuation before and after the administration of the contrast agent, and compares the attenuations. With this operation, the operator can determine whether the test site is normal.

The components of the devices in the drawings referred to in the description of the embodiments above are presented based on functional concepts, and are not necessarily physically configured as illustrated in the drawings. In other words, the specific modes of distribution and integration of the components are not limited to those illustrated in the drawings. All or part of the components can be functionally or physically distributed or integrated in any units depending on various loads and the status of use. Further, all or certain part of the processing functions performed in the components may be implemented by a CPU and a computer program that is analyzed and executed by the CPU or may be implemented as hardware using wired logic.

The control method described in the embodiments above can be implemented by having a computer such as a personal computer or a work station execute a control program prepared in advance. The control program can be distributed via a network such as the Internet. The control program is recorded in a computer-readable recording medium such as a hard disk, a flexible disk (FD), compact disc read only memory (CD-ROM), a magneto-optical (MO), and a digital versatile disc (DVD), and can be executed by being read by a computer from the recording medium.

Signal Processing Device

As described above, the signal processing method described in the first and the second embodiments and the modifications thereof is performed by the ultrasonic diagnostic apparatus. However, the signal processing method described in the first and the second embodiments and the modifications thereof may be performed by a signal processing device that can acquire signals received by the ultrasonic probe 1. The ultrasonic diagnostic apparatus may include the signal processing device that performs the signal processing method described in the first and the second embodiments and the modifications thereof.

According to at least one of the embodiments above, attenuation of echoes can be quantified with a simple configuration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A signal processing device comprising:
adjustment circuitry configured to adjust a first received signal based on a first echo of a first ultrasonic wave transmitted to a subject with first gain corresponding to a location at which the first echo and has been generated, and a second received signal based on a second echo of a second ultrasonic wave transmitted to the subject with second gain corresponding to a location at which the second echo has been generated, wherein the first ultrasonic wave is different from the second ultrasonic wave; and
processing circuitry configured (1) to limit a reception bandwidth of the second received signal to a reception bandwidth narrower than a reception bandwidth of the first received signal, (2) to correct only the second received signal among the first received signal and the second received signal that has been adjusted by the adjustment circuitry such that the gain adjustment with the second gain is canceled, (3) to calculate an index value relating to attenuation by using the corrected second received signal, and (4) to generate a B-mode image by using the first received signal that has been adjusted by the adjustment circuitry.

2. The signal processing device according to claim 1, wherein the processing circuitry corrects the second received signal that has been adjusted by the adjustment circuitry such that the processing circuitry cancels an adjustment value with which the adjustment circuitry has adjusted the second received signal.

3. The signal processing device according to claim 2, wherein the processing circuitry corrects the corrected second received signal that has been corrected in accordance with the gain in accordance with an acoustic field such that the transmitted ultrasonic waves at a focal position have the same intensity as that of the transmitted ultrasonic waves at other positions out of the focal position in the same scan line, and calculates the index value by using the second received signal that has been corrected in accordance with the gain and further corrected in accordance with the acoustic field.

4. The signal processing device according to claim 1, wherein the processing circuitry corrects the second received signal that has been adjusted by the adjustment circuitry such that the processing circuitry equalizes an adjustment value with which the adjustment circuitry has adjusted the second received signal, the adjustment value corresponding to the location at which the echo has been generated.

5. The signal processing device according to claim 4, wherein the processing circuitry corrects the corrected second received signal that has been corrected in accordance with the gain in accordance with an acoustic field such that the transmitted ultrasonic waves at a focal position have the same intensity as that of the transmitted ultrasonic waves at other positions out of the focal position in the same scan line, and calculates the index value by using the second received signal that has been corrected in accordance with the gain and further corrected in accordance with the acoustic field.

6. The signal processing device according to claim 1, wherein the processing circuitry corrects the corrected second received signal that has been corrected in accordance with the gain in accordance with an acoustic field such that the transmitted ultrasonic waves at a focal position have a same intensity as that of the transmitted ultrasonic waves at other positions out of the focal position in a same scan line, and calculates the index value by using the second received signal that has been corrected in accordance with the gain and further corrected in accordance with the acoustic field.

7. The signal processing device according to claim 1, wherein the index value is an attenuation constant.

8. The signal processing device according to claim 1, wherein the processing circuitry generates an attenuation image based on index values corresponding to a plurality of locations at which echoes have been generated, and displays the generated attenuation image on a display.

9. The signal processing device according to claim 8, wherein the processing circuitry generates a B-mode image by using the first received signal that has been adjusted by the adjustment circuitry, and displays the attenuation image on the generated B-mode image.

10. The signal processing device according to claim 9, wherein the processing circuitry generates the attenuation image by using the second received signal, and frequency components are used for generating the B-mode image.

11. The signal processing device according to claim 10, wherein the second received signal is a received signal based on an echo of an ultrasonic wave transmitted in a narrow transmission bandwidth including a center frequency.

12. The signal processing device according to claim 11, wherein the transmission bandwidth is determined based on a frequency characteristic of a probe.

13. The signal processing device according to claim 8, wherein the processing circuitry generates a B-mode image by using the first received signal, and displays the attenuation image on the generated B-mode image.

14. The signal processing device according to claim 1, wherein the processing circuitry calculates a representative value by using index values corresponding to a plurality of locations at which echoes have been generated, and displays the calculated representative value on a display.

15. The signal processing device according to claim 1, wherein
the adjustment circuitry adjusts the first received signal and the second received signal output from a plurality of transducer elements with gain,
the signal processing device further comprising delay addition circuitry configured to perform delay addition processing on the first received signal and the second received signal that have been adjusted by the adjustment circuitry, and
the processing circuitry corrects the second received signals after the delay addition processing in accordance with the gain, and calculates index values by using the corrected received signals.

16. An ultrasonic diagnostic apparatus comprising the signal processing device according to claim 1.

17. A method comprising:
adjusting a first received signal based on a first echo of a first ultrasonic wave transmitted to a subject with first gain corresponding to a location at which the first echo and has been generated, and a second received signal based on a second echo of an a second ultrasonic wave transmitted to a the subject with second gain corresponding to a location at which the second echo has been generated, wherein the first ultrasonic wave is different from the second ultrasonic wave; and
limiting a reception bandwidth of the second received signal to a reception bandwidth narrower than a reception bandwidth of the first received signal;
correcting only the adjusted second received signal from among the adjusted first and second received signals such that the gain adjustment with the second gain is canceled;
calculating an index value relating to attenuation by using the corrected second received signal; and
generating a B-mode image by using the adjusted first received signal.

18. A signal processing device comprising:
adjustment circuitry configured to adjust a first received signal based on a first echo of a first ultrasonic wave transmitted to a subject with first gain corresponding to a location at which the first echo and has been generated, and a second received signal based on a second echo of a second ultrasonic wave transmitted to the subject with second gain corresponding to a location at which the second echo has been generated, wherein the first ultrasonic wave is different from the second ultrasonic wave; and
processing circuitry configured to correct only the second received signal among the first received signal and the second received signal that has been adjusted by the adjustment circuitry such that the gain adjustment with the second gain is canceled, and to correct the second received signal in accordance with an acoustic field determined by at least one of a transmission condition of the second ultrasonic wave and a reception condition of the second echo, and to calculate an index value relating to attenuation by using the corrected received signal that has been corrected in accordance with the gain and the acoustic field.

19. The signal processing device according to claim 18, wherein the processing circuitry configured to correct the corrected second received signal that has been corrected in accordance with the gain in accordance with the acoustic field such that the transmitted ultrasonic waves at the focal position have the same intensity as that of the transmitted ultrasonic waves at other positions out of the focal position in the same scan line, and calculates the index value by using the second received signal that has been corrected in accordance with the gain and further corrected in accordance with the acoustic field.

* * * * *